US012710416B2

(12) United States Patent
Yasuura et al.

(10) Patent No.: US 12,710,416 B2
(45) Date of Patent: Aug. 18, 2026

(54) TARGET SUBSTANCE DETECTION DEVICE AND TARGET SUBSTANCE DETECTION METHOD USING MAGNETIC FIELD AND GRAVITY

(71) Applicant: NATIONAL INSTITUTE OF ADVANCED INDUSTRIAL SCIENCE AND TECHNOLOGY, Tokyo (JP)

(72) Inventors: Masato Yasuura, Ibaraki (JP); Hiroki Ashiba, Ibaraki (JP); Makoto Fujimaki, Ibaraki (JP); Takashi Fukuda, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 967 days.

(21) Appl. No.: 17/914,189

(22) PCT Filed: Jan. 20, 2021

(86) PCT No.: PCT/JP2021/001897

§ 371 (c)(1),
(2) Date: May 17, 2023

(87) PCT Pub. No.: WO2021/192555

PCT Pub. Date: Sep. 30, 2021

(65) Prior Publication Data

US 2023/0273196 A1 Aug. 31, 2023

(30) Foreign Application Priority Data

Mar. 26, 2020 (JP) ................................ 2020-055709

(51) Int. Cl.

| | |
|---|---|
| ***G01N 33/543*** | (2006.01) |
| ***B01L 3/00*** | (2006.01) |
| ***G01N 1/40*** | (2006.01) |
| ***G01N 21/64*** | (2006.01) |

(52) U.S. Cl.

CPC .. *G01N 33/54326* (2013.01); *B01L 3/502761* (2013.01); *G01N 1/40* (2013.01); *G01N 21/6428* (2013.01); *G01N 33/54386* (2013.01); *B01L 2200/0668* (2013.01); *B01L 2300/0654* (2013.01); *B01L 2400/043* (2013.01); *G01N 2001/4038* (2013.01); *G01N 2021/6439* (2013.01)

(58) Field of Classification Search

None

See application file for complete search history.

(56) References Cited

U.S. PATENT DOCUMENTS

| | | | | |
|---|---|---|---|---|
| 5,238,810 | A * | 8/1993 | Fujiwara | G01N 33/54373 436/805 |
| 5,252,493 | A | 10/1993 | Fujiwara et al. | |
| 2004/0115709 | A1 * | 6/2004 | Morozov | G01N 33/561 436/526 |
| 2010/0148768 | A1 * | 6/2010 | Schwarz | B82Y 25/00 324/239 |
| 2013/0017538 | A1 * | 1/2013 | Ionescu-Zanetti | B03C 1/288 435/6.12 |
| 2018/0372593 | A1 | 12/2018 | Templier et al. | |
| 2019/0154580 | A1 | 5/2019 | Yasuura et al. | |
| 2020/0016588 | A1 | 1/2020 | Yasuura et al. | |

FOREIGN PATENT DOCUMENTS

| | | | | |
|---|---|---|---|---|
| CN | 109154561 | A | 1/2019 | |
| JP | H04-102062 | A | 4/1992 | |
| JP | H07-504987 | A | 6/1995 | |
| KR | 10-2013-0014293 | A | 2/2013 | |
| WO | WO-1988/002118 | A1 | 3/1988 | |
| WO | WO-1993/019371 | A1 | 9/1993 | |
| WO | WO2017001705 | * | 1/2017 | B03C 1/24 |
| WO | WO-2018/100779 | A1 | 6/2018 | |
| WO | WO-2018/100780 | A1 | 6/2018 | |

OTHER PUBLICATIONS

International Search Report issued in Application No. PCT/JP2021/001897, mailed Apr. 6, 2021.

(Continued)

*Primary Examiner* — Ann Montgomery

(74) *Attorney, Agent, or Firm* — MICHAEL BEST & FRIEDRICH LLP

(57) ABSTRACT

Provided is a target substance detection device that can detect a target substance accurately and efficiently and can be manufactured at low costs. A target substance detection device 10 includes: a liquid sample storage unit 15 that is partially or wholly formed of a transparent member, and includes a storage unit formed so as to be open at a top surface thereof and configured to store a liquid sample S containing a fluorescent substance and magnetic particles that form a conjugate with a target substance; a sensing plate 11 composed of a silicon flat plate whose bottom surface is a smooth surface, the bottom surface being joined to the top surface of the liquid sample storage unit 15; a light irradiation unit 12 configured to irradiate the bottom surface of the sensing plate 11 with light including an excitation wavelength of the fluorescent substance, via the liquid sample storage unit 15; and a magnetic field application unit 14 located on a top surface side of the sensing plate 11, and configured to move a permanent magnet in a direction having a vector component in a direction parallel to an in-plane direction of the bottom surface of the sensing plate 11 in a state in which a magnetic field is applied to the conjugate in the liquid sample S stored in the storage unit.

9 Claims, 11 Drawing Sheets

(56) References Cited

OTHER PUBLICATIONS

Office Action in Chinese Application No. 202180016883.3, dated Apr. 30, 2025.

* cited by examiner

TARGET SUBSTANCE DETECTION DEVICE AND TARGET SUBSTANCE DETECTION METHOD USING MAGNETIC FIELD AND GRAVITY

TECHNICAL FIELD

The present invention relates to a target substance detection device and a target substance detection method that detect a target substance based on optical signals that is based on a conjugate obtained by binding magnetic particles to the target substance.

BACKGROUND ART

In recent years, methods have been developed to detect and determine, as a target substance, a micro substance present in a solution, in particular a bio-related substance such as DNA, RNA, protein, virus, or bacteria.

As one of the methods for detecting and determining the bio-related substance, a fluorescence immunoassay (FIA) is widely used. In the FIA method, an antibody that specifically binds to a target substance such as specific bacteria and virus is used to bind a fluorescent dye, and light emission of the fluorescent dye is observed using a fluorescent microscope or the like to detect and determine the target substance.

However, the fluorescence immunoassay requires multiple reaction steps and repeated washing steps, and needs a lot of time and effort to obtain measurement results. Moreover, further improvement in detection sensitivity is needed.

To improve the detection accuracy in detecting a target substance using the foregoing bio-related substance detection methods, a measurement method using magnetic particles has been proposed. For example, the following detection method has been disclosed: A conjugate containing a target substance and magnetic particles is gathered to the bottom of a liquid sample container, and fixed to the bottom of the container by an antigen-antibody reaction between the conjugate and an antibody placed on the bottom of the container (see Patent Document 1).

Such a measurement method using magnetic particles improves the detection sensitivity by the concentration effect of gathering the conjugate at a detection position on the liquid sample bottom by a magnetic field. With this method, however, it is impossible to distinguish the optical signals based on the conjugate from noise signals caused by impurities floating at the concentrated detection position, impurities adsorbed to the bottom of the liquid sample container, scratches on the bottom of the liquid sample container, fluctuation of output of a light source of detection light used for detection, and the like. Thus, the method has a problem of low detection accuracy. This problem is more noticeable in the case of detecting a micro substance.

To remove the noise signals based on impurities adsorbed to the bottom of the liquid sample container, a washing process of removing impurities needs to be performed in each detection operation. This causes low detection efficiency.

To solve these problems, the present inventors have proposed an external force support type sensor which is a target substance detection device including a magnetic field application unit (see Patent Documents 2 and 3). According to this proposal, a photodetector is used to observe the movement of a conjugate that is obtained by binding magnetic particles which move with the application of a magnetic field from the magnetic field application unit, a photoresponsive substance (a fluorescent substance, etc.) which emits the optical signals, and a target substance, to distinguish the optical signals (positive signals) based on the conjugate from the noise signals caused by impurities floating at the detection position, impurities adsorbed to the bottom of the liquid sample container, scratches on the bottom of the liquid sample container, fluctuation of output of a light source of detection light used for detection, and the like.

Thus, utilizing the phenomenon that the magnetic field application causes the positive signals to move but does not cause the noise signals and the like to move, the external force support type sensor observes the movement of the detected optical signals and distinguishes whether the optical signals result from the conjugate or result from the noise signals or the like. In this way, the detection accuracy and the detection efficiency are improved.

However, the external force support type sensor has been found to have the following problem. This will be described in detail below, with reference to FIG. 1 and FIG. 2. FIG. 1 is an explanatory drawing for explaining a conventional external force support type sensor. FIG. 2 is an explanatory drawing for explaining the behavior of particles on a sensing plate in the external force support type sensor illustrated in FIG. 1.

As illustrated in FIG. 1, an external force support type sensor 100 is configured in conformity with a vertical illumination type microscope, and includes a sensing plate 101, a light irradiation unit 102, an optical signal detection unit 103, and a magnetic field application unit 104.

A liquid sample subjected to detection is introduced onto the top surface of the sensing plate 101, covered with a cover glass or the like, and held on the top surface of the sensing plate 101.

As the sensing plate 101, a glass plate, a plastic plate, or a metal plate employed in a microscope observation stage is used.

The optical signal detection unit 103 includes a half mirror 103*a*, an objective lens 103*b*, and an imaging device 103*c*. The optical signal detection unit 103 guides light L emitted from the light irradiation unit 102 onto the sensing plate 101, and detects the optical signals in a detection region (an observation region) on the top surface of the sensing plate 101 generated based on the irradiation with the light L. The imaging device 103*c* includes a CCD image sensor or the like, and is configured to acquire a two-dimensional image of the detection region.

The magnetic field application unit 104 includes a permanent magnet and a sliding member slidable in $X_1$ or $X_2$ direction parallel to the in-plane direction of the sensing plate 101 while holding the permanent magnet.

In the external force support type sensor 100 having this structure, optical signals (positive signals) based on a conjugate in the liquid sample introduced onto the sensing plate 101 are moved to follow the movement of the magnetic field application unit 104 (in $X_1$ or $X_2$ direction), and detected as distinguished from the noise signals or the like which is unmoving optical signals.

The liquid sample introduced and held on the top surface of the sensing plate 101 contains a target substance, magnetic particles that bind to the target substance, a photoresponsive substance that binds to the target substance, an impurity, and the like. The magnetic particles include those bound to the target substance to form the conjugate and those unbound to the target substance. The photoresponsive substance includes those bound to the target substance to form the conjugate and those unbound to the target substance.

In a scene of detection by the external force support type sensor 100, the magnetic field application unit 104 is located at an initial position on the bottom surface side of the sensing plate 101, and the conjugate is concentrated in the detection region on the top surface of the sensing plate 101. After this, the magnetic field application unit 104 is moved (in $X_1$ or $X_2$ direction) to move the conjugate. The problem that occurs here will be described below, with reference to FIG. 2.

In the scene of detection by the external force support type sensor 100, at the initial position of the magnetic field application unit 104, gravitationally sedimented impurity I and an unbound fluorescent substance F are present on the top surface of the sensing plate 101. Unbound magnetic particles M attracted to the detection region on the top surface of the sensing plate 101 by the magnetic field application from the magnetic field application unit 104 are also present on the top surface of the sensing plate 101. Target substance T is interposed between magnetic particles M and a fluorescent substance F to form the conjugate, and is attracted to the detection region on the top surface of the sensing plate 101 by the magnetic field application from the magnetic field application unit 104 and is present in the detection region.

When the magnetic field application unit 104 moves subsequently, the conjugate moves to follow the movement of the magnetic field application unit 104 as indicated by "A" in FIG. 2, and generates the positive signals.

However, if there is the impurity I non-specifically adsorbed to the top surface of the sensing plate 101 as indicated by "B" in FIG. 2, the movement of the conjugate to follow the movement of the magnetic field application unit 104 is hindered. This makes it impossible to detect as distinguished from the noise signals or the like which are the unmoving optical signals.

Moreover, the unbound magnetic particles M that move to follow the movement of the magnetic field application unit 104 move while involving the unbound fluorescent substance F as indicated by "C" in FIG. 2. As a result of that, moving optical signals (false positive signals) are generated despite target substance T not being present.

Thus, in the external force support type sensor 100, there is a risk that positive signals cannot be correctly detected due to the optical signals of types "B" and "C", and consequently the detection accuracy decreases.

PRIOR ART DOCUMENTS

Patent Documents

Patent Document 1: Japanese Patent Application Laid-Open No. H4(1992)-102062

Patent Document 2: International Patent Application Publication No. 2018/100779

Patent Document 3: International Patent Application Publication No. 2018/100780

SUMMARY OF THE INVENTION

Problems to be Solved by the Invention

The present invention has an object of solving the problems of the conventional techniques and providing a target substance detection device that can detect a target substance accurately and efficiently and can be manufactured at low costs, and a target substance detection method using the same.

Upon careful examination to solve the problems stated above, the present inventors obtained the following findings.

The decrease in the detection accuracy of the external force support type sensor 100 is caused by the impurity I and the unbound fluorescent substance F gravitationally sedimented on the top surface of the sensing plate 101 (see FIG. 2).

In view of this, the present inventors conceived a structure in which the surface of the sensing plate 101 on which the liquid sample is introduced and held is vertically inverted to change it from the top surface to the bottom surface and the arrangement of the light irradiation unit 102, the optical signal detection unit 103, and the magnetic field application unit 104 with respect to the sensing plate 101 is vertically inverted to change it from the upright arrangement to the inverted arrangement.

With this structure, in the liquid sample introduced and held on the bottom surface of the sensing plate 101, the gravitationally sedimented impurity I and the unbound fluorescent substance F are separate from the conjugate and unbound magnetic particles M attracted to the bottom surface of the sensing plate 101 against gravity by the magnetic field application from the magnetic field application unit 104. Hence, the decrease in detection accuracy due to the impurity I and the fluorescent substance F can be prevented.

In this structure, however, it is necessary to apply a magnetic field stronger than the magnetic field applied in the upright arrangement, for the purpose of attracting the conjugate and the like to the bottom surface of the sensing plate 101 against gravity. In the case where a glass plate is used as the sensing plate 101 in accordance with conventional examples, the movement of the conjugate is hindered as the conjugate is caught on the glass plate due to the roughness of the glass plate.

The present inventors then examined the structural materials of the sensing plate 101, and found out the following: In the case where the glass plate is transparent, the light L emitted from the light irradiation unit 102 becomes stray light and is detected by the optical signal detection unit 103. This tends to cause whiteout of the conjugate detected as bright spots.

In the case where a plastic plate is used as the sensing plate 101 in accordance with conventional examples, if the plastic plate is transparent, whiteout of the conjugate tends to occur as in the case of the glass plate. If the plastic plate is also opaque, whiteout of the conjugate tends to occur due to autofluorescence.

In the case where a metal plate is used as the sensing plate 101 in accordance with conventional examples, the metal plate itself is magnetized by the magnetic field application unit 104 due to its forming materials and hinders the movement of the conjugate, or the metal plate serves as a magnetic shield of the magnetic field applied to the conjugate from the magnetic field application unit 104 and hinders the movement of the conjugate.

The present inventors then searched for new structural materials of the sensing plate 101, and eventually found out that, by using a silicon flat plate having a smooth surface, the positive signals generated as a result of the movement of the conjugate can be detected accurately. Since silicon flat plates are widely used as semiconductor materials and the like and can be obtained at low costs, the manufacturing costs can be reduced.

Means for Solving the Problems

The present invention is based on these findings. Means for solving the problems stated above are as follows:

<1> A target substance detection device including: a liquid sample storage unit that is partially or wholly formed of a transparent member, and includes a storage unit formed so as to be open at a top surface thereof and configured to store a liquid sample containing a fluorescent substance and magnetic particles that form a conjugate with a target substance; a sensing plate composed of a silicon flat plate whose bottom surface is a smooth surface, the bottom surface being joined to the top surface of the liquid sample storage unit; a light irradiation unit configured to irradiate the bottom surface of the sensing plate with light including an excitation wavelength of the fluorescent substance, via the liquid sample storage unit; and a magnetic field application unit located on a top surface side of the sensing plate, and configured to move a permanent magnet in a direction having a vector component in a direction parallel to an in-plane direction of the bottom surface of the sensing plate in a state in which a magnetic field is applied to the conjugate in the liquid sample stored in the storage unit.

<2> The target substance detection device according to <1>, wherein a maximum height roughness Rz indicating roughness of the smooth surface is 63.3 nm or less.

<3> The target substance detection device according to <1> or <2>, wherein the permanent magnet includes any of a first shape portion and a second shape portion, the first shape portion being a portion of an overall approximately protrusion strip shape in which a tip part smaller in diameter than a base protrudes from the base and is located on a side closer to the sensing plate, and the second shape portion being a portion of an approximately cone shape or an approximately truncated cone shape tapered toward the sensing plate.

<4> The target substance detection device according to any of <1> to <3>, including a magnetic shield member configured to be interposed between the sensing plate and the magnetic field application unit as a result of movement of the magnetic shield member or the magnetic field application unit.

<5> The target substance detection device according to any of <1> to <4>, including an optical signal detection unit located on a bottom surface side of the sensing plate, and configured to detect fluorescence emitted from the fluorescent substance.

<6> The target substance detection device according to <5>, wherein the optical signal detection unit includes an optical filter configured to transmit light included in a wavelength band of the fluorescence emitted from the fluorescent substance.

<7> The target substance detection device according to any of <1> to <6>, wherein the smooth surface is surface-modified with a coating agent that suppresses adsorption of the conjugate.

<8> The target substance detection device according to any of <1> to <7>, wherein the liquid sample storage unit includes a liquid sample flow path connecting an outside of the liquid sample storage unit and the storage unit.

<9> A target substance detection method of detecting a target substance using the target substance detection device according to any of <1> to <8>, the target substance detection method including: a liquid sample storage step of storing, in the storage unit in the liquid sample storage unit, a liquid sample containing a fluorescent substance and magnetic particles that form a conjugate with a target substance; a separation step of placing the magnetic field application unit at an initial position on the top surface side of the sensing plate, and attracting the conjugate in the liquid sample to the bottom surface of the sensing plate to separate the conjugate from gravitational sediments in the liquid sample; a light irradiation step of irradiating the bottom surface of the sensing plate with light including an excitation wavelength of the fluorescent substance from the light irradiation unit via the liquid sample storage unit; and a conjugate moving step of, in a state in which the bottom surface of the sensing plate is irradiated with the light, moving the magnetic field application unit from the initial position in a direction having a vector component in a direction parallel to an in-plane direction of the bottom surface of the sensing plate, to move the conjugate attracted to the bottom surface of the sensing plate in the direction parallel to the in-plane direction of the bottom surface.

Advantageous Effect of the Invention

According to the present invention, it is possible to solve the problems of the conventional techniques and provide a target substance detection device that can detect a target substance accurately and efficiently and can be manufactured at low costs, and a target substance detection method using the same.

BRIEF DESCRIPTION OF THE DRAWINGS

FIG. 7(*b*) is a view (2) showing an example of the structure of a magnetic field application unit having a first shape portion.

FIG. 7(*c*) is a view (3) showing an example of the structure of a magnetic field application unit having a first shape portion.

FIG. 7(*d*) is a view (1) showing an example of the structure of a magnetic field application unit having a second shape portion.

FIG. 7(*e*) is a view (2) showing an example of the structure of a magnetic field application unit having a second shape portion.

FIG. 11(*b*) is a view showing an imaging result obtained by adding a scattered light image to the fluorescent image as the test result of Measurement Test 2 for the target substance detection device according to Example 1.

FIG. 12(*b*) is a view showing an imaging result obtained by adding a scattered light image to the fluorescent image as the test result of Measurement Test 2 for the target substance detection device according to Comparative Example 2.

FIG. 15(*b*) is a view showing a fluorescent image 60 seconds after collection start in the target substance detection device according to Example 1.

FIG. 16(*b*) is a view showing a fluorescent image 60 seconds after collection start in the target substance detection device according to Reference Example 1.

Figure 1:
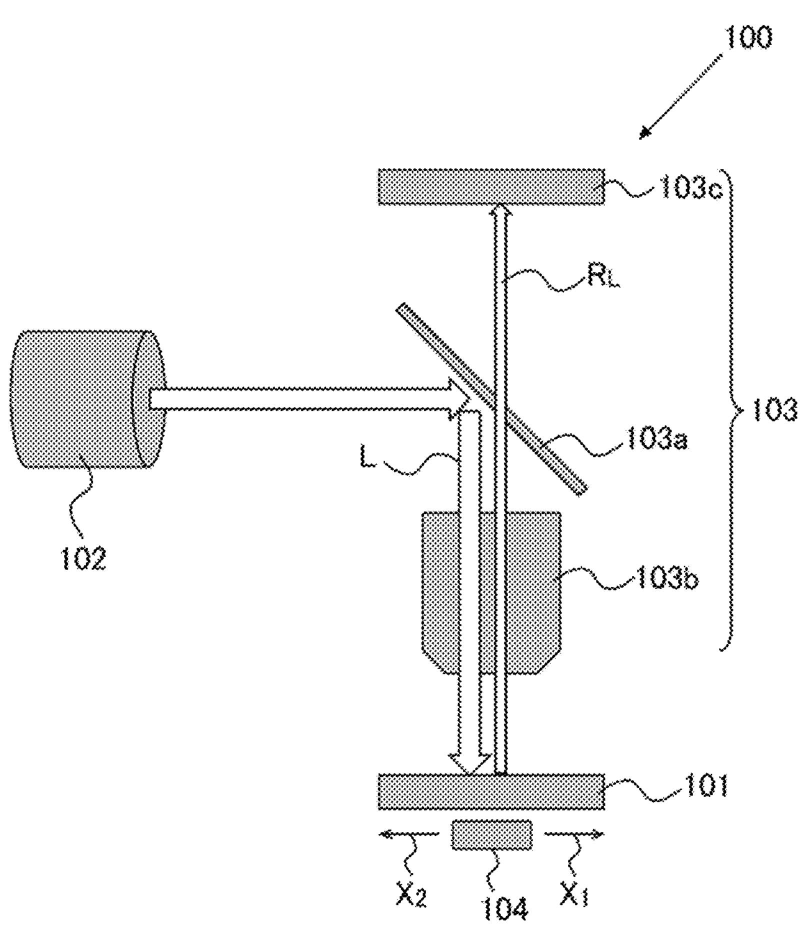
FIG. 1 is an explanatory drawing for explaining a conventional external force support type sensor.

MODE FOR CARRYING OUT THE INVENTION (Target Substance Detection Device)

A target substance detection device according to the present invention includes a liquid sample storage unit, a sensing plate, a light irradiation unit, and a magnetic field application unit. The target substance detection device according to the present invention includes one or more other members according to need.

<Liquid Sample Storage Unit>

The liquid sample storage unit is partially or wholly formed of a transparent member, and includes a storage unit that is open at its top surface and is configured to store a liquid sample.

The transparent member is not limited, and may be selected as appropriate according to the purpose. Examples of the transparent member include known glass materials and plastic materials.

The liquid sample storage unit is not limited, and may be selected as appropriate according to the purpose. While the liquid sample storage unit may be composed of a known box-shaped container or the like, the liquid sample storage unit preferably has a liquid sample flow path connecting the outside of the liquid sample storage unit and the storage unit. In the case of the liquid sample storage unit having the flow path, the liquid sample which may contain any harmful substance can be handled easily.

The liquid sample storage unit may include a plurality of storage units to form multiple channels.

—Liquid Sample—

The liquid sample contains magnetic particles and a fluorescent substance that form a conjugate with a target substance.

—Target Substance—

The target substance is not limited, and may be selected as appropriate according to the purpose. Examples of the target substance include DNA, RNA, proteins, viruses, bacteria, and contaminants.

Specific examples of liquid specimens subjected to target substance detection include blood, saliva, urine, chemical liquids, environmental water, water supply and sewage, beverages, homogenized solutions of foods, wiping liquids, liquids containing a solid sample, such as a powder, dissolved or suspended in a solvent such as water, and gas-phase concentrates containing trapped gas and fine particles in gas phase.

Accordingly, specific examples of the liquid sample include liquid samples obtained by adding the magnetic particles, the fluorescent substance, etc. to such liquid specimens.

—Magnetic Particles—

The magnetic particles function to form the conjugate with the target substance and move the target substance through magnetic field application from the magnetic field application unit.

The magnetic particles are not limited as long as the foregoing function is achieved, and may be selected as appropriate according to the purpose. Examples of the magnetic particles that can be used include known magnetic beads.

The method of binding the target substance and the magnetic particles is not limited, and may be selected as appropriate according to the purpose. Examples of the method that can be used include known binding methods such as physical adsorption, antigen-antibody reaction, DNA hybridization, biotin-avidin bond, chelate bond, and amino bond.

Examples of the binding method by physical adsorption include a method of binding the target substance and the magnetic particles using an electrostatic bonding force such as hydrogen bond.

Of these binding methods, a method of specifically binding the target substance and the magnetic particles by a binding method such as antigen-antibody reaction, DNA hybridization, biotin-avidin bond, chelate bond, or amino bond is preferably used in order to prevent the target substance and the magnetic particles from binding to impurities.

—Fluorescent Substance—

The fluorescent substance functions to form the conjugate with the target substance and emit fluorescence when irradiated with light emitted from the light irradiation unit. Optical signals based on this fluorescence serve as a marker for the target substance (the conjugate), and form the positive signals that indicate the detection of the target substance (the conjugate) through movement.

The fluorescent substance is not limited as long as the foregoing function is achieved, and may be selected as appropriate according to the purpose. Examples of the fluorescent substance that can be used include known fluorescent materials such as fluorescent dyes, quantum dots, fluorescence beads, quantum dot-containing beads, and fluorescence staining agents.

The method of binding the target substance and the fluorescent substance is not limited, and may be selected as appropriate according to the purpose. Examples of the method that can be used include known binding methods such as physical adsorption, antigen-antibody reaction, DNA hybridization, a biotin-avidin bond, a chelate bond, and an amino bond.

In the case of using a fluorescent dye as the fluorescent substance, dying of the target substance with the fluorescent dye is also an effective method to bind the target substance and the fluorescent substance.

Examples of the binding method by physical adsorption include a method of binding the target substance and the fluorescent substance using an electrostatic bonding force such as hydrogen bond.

Of these binding methods, a method of specifically binding the target substance and the fluorescent substance by a binding method such as the antigen-antibody reaction, the DNA hybridization, the biotin-avidin bond, the chelate bond, or the amino bond is preferably used in order to prevent the target substance and the fluorescent substance from binding to impurities.

<Sensing Plate>

The sensing plate is composed of a silicon flat plate whose bottom surface is a smooth surface, and is arranged with the bottom surface joined to the top surface of the liquid sample storage unit. Herein, the term "a silicon flat plate" includes not only a flat plate mainly made of silicon (Si), but also a plate that is obtained by forming a film mainly made of silicon on a known substrate such as glass materials or plastic materials by a known method such as sputter deposition and whose bottom surface is the film formation surface. The expression "a flat plate mainly made of silicon" means that silicon is highest in content among the components constituting the flat plate, and includes a flat plate having low content of materials other than silicon, such as impurities. Likewise, the expression "a film mainly made of silicon" means that silicon is highest in content among the components constituting the film, and includes a film having low content of materials other than silicon, such as impurities.

The thickness of the silicon flat plate is not limited, but is preferably 50 nm to 2.5 mm. If the thickness is more than 2.5 mm, the performance of collection of the conjugate to the bottom surface and the mobility of the conjugate in the vicinity of the bottom surface through magnetic field application may decrease. If the thickness is less than 50 nm, stray light caused by transmitted light may occur.

Since the sensing plate is composed of the silicon flat plate, it is possible to prevent the problem of whiteout of the positive signals caused by stray light which occurs in the case of using a transparent glass plate or a plastic plate. It is also possible to prevent the problem of whiteout of the positive signals caused by autofluorescence which occurs in the case of using opaque plastic materials. It is also possible to prevent the problem in that, in the case of using a metal plate, the metal plate itself is magnetized by the magnetic field application unit due to its forming material and hinders the movement of the conjugate, or the metal plate serves as a magnetic shield of the magnetic field applied to the conjugate from the magnetic field application unit and hinders the movement of the conjugate.

In addition, the silicon flat plate having the smooth surface allows smooth movement of the conjugate attracted to the magnetic field application unit and in close contact with the smooth surface. Moreover, the silicon flat plate is widely used as semiconductor materials and can be obtained at low costs.

Thus, one feature of the target substance detection device according to the present invention is that the silicon flat plate is used instead of a conventionally used glass plate, plastic plate, or metal plate.

Figure 2:
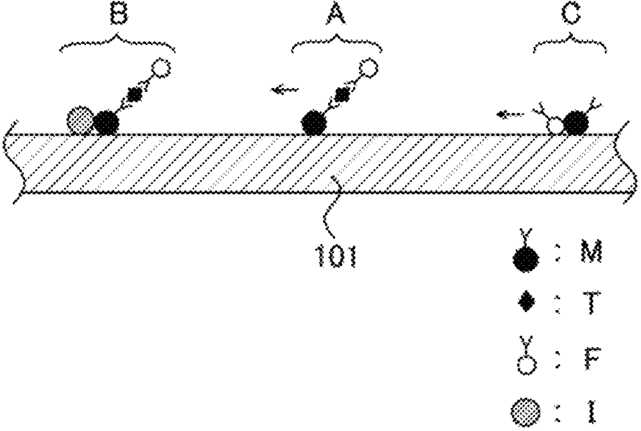
FIG. 2 is an explanatory drawing for explaining the behavior of particles on a sensing plate in the external force support type sensor illustrated in FIG. 1.

Another feature of the target substance detection device according to the present invention is a structure in which the liquid sample is placed on the bottom surface of the sensing plate. With such a structure, the conjugate attracted to the bottom surface of the sensing plate can be separated from the gravitational sediments in the liquid sample. Hence, it is possible to prevent the problem of incorrectly detecting the noise signals as the positive signals and the problem of incorrectly detecting the false positive signals as the positive signals (FIG. 2).

In view of this, the terms "a top surface" and "a bottom surface" herein are defined as follows:

The term "a top surface" denotes a surface in which the plane-perpendicular direction orthogonal to the in-plane direction is inclined to the vertically upper side from the horizontal direction. The term "a bottom surface" is defined as a surface opposite to "the top surface", and denotes a surface in which the plane-perpendicular direction orthogonal to the in-plane direction is inclined to the vertically lower side from the horizontal direction.

Regarding "the top surface", not only in the case where the in-plane direction and the horizontal direction match, i.e. the plane-perpendicular direction matches the vertically upward direction, but also even in other cases where the plane-perpendicular direction is inclined to the vertically upper side from the horizontal direction, the conjugate can be separated from the gravitational sediments in the liquid sample. Therefore, the term "a top surface" also includes the latter cases.

The roughness of the smooth surface is not limited. However, given that lower roughness allows smoother movement of the conjugate attracted to the magnetic field application unit and in close contact with the smooth surface, the roughness of the smooth surface is preferably 63.3 nm or less in maximum height roughness Rz which is an index of roughness of surface texture.

The "maximum height roughness Rz" is measured in accordance with JIS B0601-2013, and can be obtained using a known profilometer (for example, Dektak XT-S profilometer manufactured by Bruker Corporation).

The smooth surface is not limited, but is preferably surface-modified with a coating agent that suppresses adsorption of the conjugate from the viewpoint of smoothly moving the conjugate.

The coating agent is not limited, and may be selected as appropriate according to the purpose. Examples of the coating agent include known fluorine-based coating agents (for example, KY-164 manufactured by Shin-Etsu Chemical Co., Ltd.), skim milk, bovine serum albumin (BSA), and a silane-based self-assembled monolayer modified with a polyethylene glycol chain.

<Light Irradiation Unit>

The light irradiation unit is configured to irradiate the bottom surface of the sensing plate with light including the excitation wavelength of the fluorescent substance, via the liquid sample storage unit.

A light source in the light irradiation unit is not limited, and may be selected as appropriate according to the purpose. Examples of the light source that can be used include known light-emitting devices such as lamps, LED devices, and laser irradiation devices.

Optical elements other than the light source are not limited, and optical elements used in known optical microscopes may be selected as appropriate according to the purpose.

In the case where the liquid sample storage unit has a non-transparent part, the bottom surface of the sensing plate is irradiated with light from the light irradiation unit via the transparent member in the liquid sample storage unit.

<Magnetic Field Application Unit>

The magnetic field application unit is located on the top surface side of the sensing plate, and is configured to move a permanent magnet in a direction having a vector component in the direction parallel to the in-plane direction of the bottom surface of the sensing plate in a state in which a magnetic field is applied to the conjugate in the liquid sample stored in the storage unit.

The magnetic field application unit is not limited as long as the foregoing function is achieved, and may be selected as appropriate according to the purpose. For example, the magnetic field application unit may include a known permanent magnet and a known moving member that movably holds the permanent magnet.

An example of the moving method of the magnetic field application unit is a method of moving from an initial position that is a position on the top surface side of the sensing plate opposite to the position on the bottom surface side of the sensing plate to which the conjugate is attracted, to a comparative observation position shifted from the initial position in a direction having a vector component in the direction parallel to the in-plane direction of the bottom surface of the sensing plate. By comparing the optical signals at the initial position and the optical signals at the comparative observation position, the movement of the conjugate can be detected.

After the measurement, when separating the conjugate from the bottom surface of the sensing plate, the magnetic field application unit needs to be moved to such a separate position where the magnetic field does not reach the bottom surface. The separate position depends on the size and the forming materials of the permanent magnet, but is, for example, about 3 cm to 10 cm away from the bottom surface. The magnetic field application unit is preferably movable from the initial position to the separate position.

The permanent magnet is not limited, and may be selected as appropriate according to the purpose. From the viewpoint of attracting the conjugate to the bottom surface of the sensing plate against gravity, the strength of the magnetic field acting on the bottom surface is preferably high. Accordingly, the permanent magnet preferably has any of a first shape portion and a second shape portion, where the first shape portion is a portion of an overall approximately protrusion strip shape in which a tip part smaller in diameter than a base protrudes from the base and is located on the side closer to the sensing plate, and the second shape portion is a portion of an approximately cone shape or an approximately truncated cone shape tapered toward the sensing plate.

These shape portions can each be obtained by working a known permanent magnet (for example, neodymium magnet) by a known working method.

<Other Members>

Other members may be selected as appropriate according to the purpose, unless the effects according to the present invention are not hindered. Examples of the other members include an optical signal detection unit, a magnetic shield member, and any members used in known transmission microscopes, known vertical illumination type microscopes, and the like.

—Optical Signal Detection Unit—

The optical signal detection unit is located on the bottom surface side of the sensing plate, and is configured to detect fluorescence emitted from the fluorescent substance.

The optical signal detection unit is an essential component in target substance detection operation. However, since an existing optical signal detection unit possessed by a user who performs target substance detection can be used, the optical signal detection unit is not an essential component in the target substance detection device.

On the other hand, if the optical signal detection unit is integrally included in the target substance detection device, the target substance detection device is more convenient and preferable.

The optical signal detection unit is not limited, and may be selected as appropriate according to the purpose. The optical signal detection unit may include a known photodetector such as a photodiode or a photomultiplier, and a known optical element such as an objective lens.

The optical signal detection unit is preferably configured to acquire the state of a detection region (an observation region) on the bottom surface of the sensing plate as a two-dimensional image, without being limited thereto. Such a two-dimensional image enables easy acquisition of the positional information or the size information on the optical signals in the two-dimensional image that appear as the bright spots. Comparison of the two-dimensional images before and after the movement of the conjugates enables clear distinction about whether the optical signals are information relating to the conjugate or information not relating to the conjugate but relating to scratches on the bottom surface of the sensing plate, fluctuation in the output of the light source, or the like. To obtain such two-dimensional image information, an imaging device may be selected as the optical signal detection unit.

The imaging device is not limited, and may be selected as appropriate according to the purpose. Examples of the imaging device that can be used include known image sensors such as a CCD image sensor and a CMOS image sensor.

Detection of the target substance includes detection of whether the target substance is present, detection of the amount of the target substance (quantitative measurement), and real-time observation of the state of the presence of the target substance.

The optical signal detection unit preferably includes an optical filter configured to transmit light included in the wavelength band of the fluorescence emitted from the fluorescent substance, without being limited thereto.

With such an optical filter, the fluorescence emitted from the fluorescent substance contained in the conjugate can be distinguished from scattered light from the magnetic particles attracted to the bottom surface of the sensing plate, so that the conjugate detection accuracy can be improved.

—Magnetic Shield Member—

The magnetic shield member is used to separate the conjugate from the bottom surface of the sensing plate after the measurement, and is formed of known magnetic shield materials.

When the magnetic shield member is provided and configured to be interposed between the sensing plate and the magnetic field application unit as a result of the movement of the magnetic shield member or the movement of the magnetic field application unit, the conjugate can be separated from the bottom surface of the sensing plate after the measurement.

With such a structure, the device can be reduced in size. In the case where the magnetic shield member is not provided, the conjugate is separated from the bottom surface of the sensing plate by moving the magnetic field application unit to the separate position about 3 cm to 10 cm away from the bottom surface of the sensing plat. In this case, the size of the device is likely to be larger. In the case where the magnetic shield member is provided, on the other hand, the magnetic shield member is interposed between the sensing plate and the magnetic field application unit to block the magnetic field. Hence, the moving distance can be reduced.

(Target Substance Detection Method)

A target substance detection method according to the present invention is a method of detecting a target substance using the target substance detection device according to the present invention. The target substance detection method according to the present invention includes a liquid sample storage step, a separation step, a light irradiation step, and a conjugate moving step, and may further includes an optical signal detection step as a step in a target substance detection scene.

<Liquid Sample Storage Step>

The liquid sample storage step is a step of storing, in the storage unit in the liquid sample storage unit, a liquid sample containing a fluorescent substance and magnetic particles that form a conjugate with a target substance.

The liquid sample storage step can be carried out by applying the matters described regarding the target substance detection device according to the present invention.

<Separation Step>

The separation step is a step of placing the magnetic field application unit at the initial position on the top surface side of the sensing plate and attracting the conjugate in the liquid sample to the bottom surface of the sensing plate to separate the conjugate from the gravitational sediments in the liquid sample.

The separation step can be carried out by applying the matters described regarding the target substance detection device according to the present invention.

<Light Irradiation Step>

The light irradiation step is a step of irradiating the bottom surface of the sensing plate with light including the excitation wavelength of the fluorescent substance from the light irradiation unit via the liquid sample storage unit.

The light irradiation step can be carried out by applying the matters described regarding the target substance detection device according to the present invention.

<Conjugate Moving Step>

The conjugate moving step is a step of moving the magnetic field application unit from the initial position in a direction having a vector component in the direction parallel to the in-plane direction of the bottom surface of the sensing plate in a state in which the bottom surface of the sensing plate is irradiated with the light, to move the conjugate attracted to the bottom surface of the sensing plate in the direction parallel to the in-plane direction of the bottom surface.

The conjugate moving step can be carried out by applying the matters described regarding the target substance detection device according to the present invention.

<Optical Signal Detection Step>

The optical signal detection step is a step of detecting a change in the optical signals based on the movement of the magnetic field application unit.

The optical signal detection step can be carried out by applying the matters described regarding the target substance detection device according to the present invention.

The target substance detection device and the target substance detection method according to the present invention will be described in more detail below, with reference to the drawings.

First Embodiment

Figure 3:
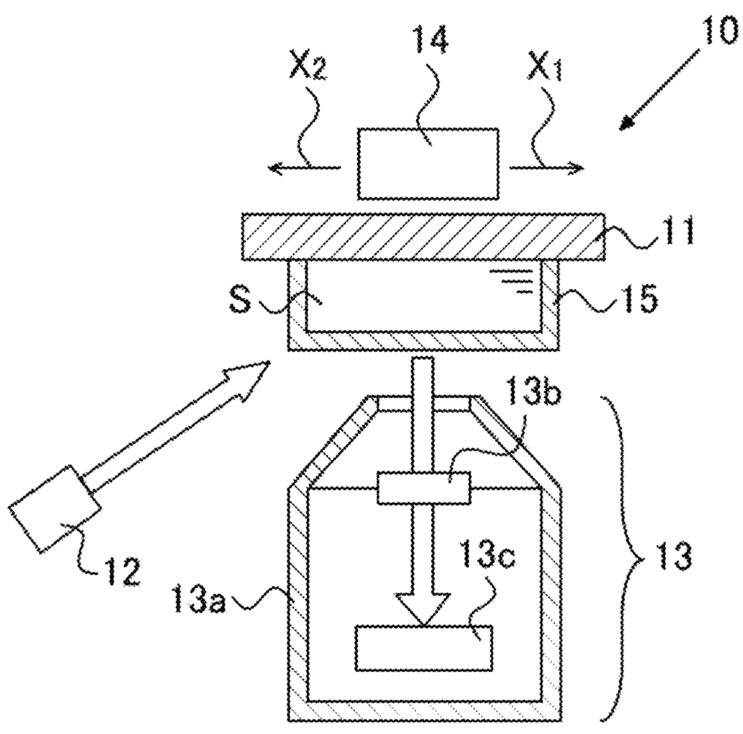
FIG. 3 is a partial sectional drawing illustrating a scheme of a target substance detection device according to a first embodiment of the present invention.

A target substance detection device according to a first embodiment of the present invention will be described below, with reference to FIG. 3. FIG. 3 is a partial sectional drawing illustrating a scheme of the target substance detection device according to the first embodiment of the present invention.

As illustrated in FIG. 3, a target substance detection device 10 includes a sensing plate 11, a light irradiation unit 12, an optical signal detection unit 13, a magnetic field application unit 14, and a liquid sample storage unit 15.

The liquid sample storage unit 15 is formed of the transparent member at least in a part that transmits light emitted from the light irradiation unit 12 and the optical signals to the optical signal detection unit 13, and is configured as an overall approximately box-shaped storage unit for storing a liquid sample S in a state of being open at the top surface.

The sensing plate 11 is composed of the silicon flat plate whose bottom surface is a smooth surface, and the bottom surface is joined to the top surface of the liquid sample storage unit 15. That is, the sensing plate 11 and the liquid sample storage unit 15 are configured so that the liquid surface of the liquid sample S and the bottom surface of the sensing plate 11 are in contact with each other in a state in which the storage unit is filled with the liquid sample S.

The light irradiation unit 12 is composed of a known light source and the like, and is configured to irradiate the bottom surface of the sensing plate 11 with light including the excitation wavelength of the fluorescent substance via the liquid sample storage unit 15.

The optical signal detection unit 13 is located on the bottom surface side of the sensing plate 11, and has a structure in which an optical filter 13*b* and an imaging device 13*c* are arranged in a housing 13*a* as a darkroom in this order from the side closer to the sensing plate 11. The optical filter 13*b* is composed of a known optical filter for transmitting light included in the wavelength band of the fluorescence emitted from the fluorescent substance. The imaging device 13*c* is composed of a known CCD image sensor and the like, and is configured to acquire a two-dimensional image.

In the optical signal detection unit 13 having this structure, there is cut the scattered light emitted from the magnetic particles, and the fluorescence emitted from the fluorescent substance can be detected as the bright spots shown in the two-dimensional image.

The arrangement configuration of the sensing plate 11, the light irradiation unit 12, and the optical signal detection unit 13 conforms to the arrangement configuration of a known inverted microscope, but differs from the arrangement configuration of a known inverted microscope in that the liquid sample storage unit 15 is joined to the bottom surface of the sensing plate 11.

The magnetic field application unit 14 is located on the top surface side of the sensing plate 11. The magnetic field application unit 14 includes a known permanent magnet, and is configured to move, by a moving mechanism such as a known sliding member, the permanent magnet in a direction having a vector component in the direction parallel to the in-plane direction of the bottom surface of the sensing plate 11 in a state in which a magnetic field is applied to the conjugate in the liquid sample S stored in the storage unit.

In this embodiment, the magnetic field application unit 14 is movable from an initial position in $X_1$ or $X_2$ direction, where the initial position is a position facing a detection region that is the position on the bottom surface of the sensing plate 11 irradiated with light from the light irradiation unit 12.

The target substance detection device 10 detects the target substance in the following manner:

First, the liquid sample S containing the magnetic particles and the fluorescent substance that form the conjugate with the target substance is stored in the storage unit (a liquid sample storage step).

Next, the magnetic field application unit 14 is placed at the initial position, and the conjugate floating in the liquid phase of the liquid sample S is attracted to the bottom surface of the sensing plate 11 to separate the conjugate from the gravitational sediments in the liquid sample S (a separation step). The gravitational sediments include impurities and the fluorescent substance unbound to the target substance.

Next, the bottom surface of the sensing plate 11 is irradiated with light including the excitation wavelength of the fluorescent substance, from the light irradiation unit 12 via the liquid sample storage unit 15 (a light irradiation step).

Next, in a state in which the bottom surface of the sensing plate 11 is irradiated with the light, the magnetic field application unit 14 is moved from the initial position in a direction having a vector component in the direction parallel to the in-plane direction of the bottom surface of the sensing plate, to move the conjugate attracted to the bottom surface of the sensing plate 11 in the direction parallel to the in-plane direction of the bottom surface (a conjugate moving step).

Concurrently with the light irradiation step and the conjugate moving step, the optical signal detection unit 13 performs optical signal detection, and detects the fluorescence emitted from the fluorescent substance to detect a change in the optical signals based on the movement of the magnetic field application unit 14 (an optical signal detection step). The change in the optical signals may include not only the change when comparing the optical signals before and after the movement of the magnetic field application unit 14 but also the temporal change when comparing the optical signals at one point in time and the optical signals at another subsequent point in time for the moving magnetic field application unit 14.

Figure 4:
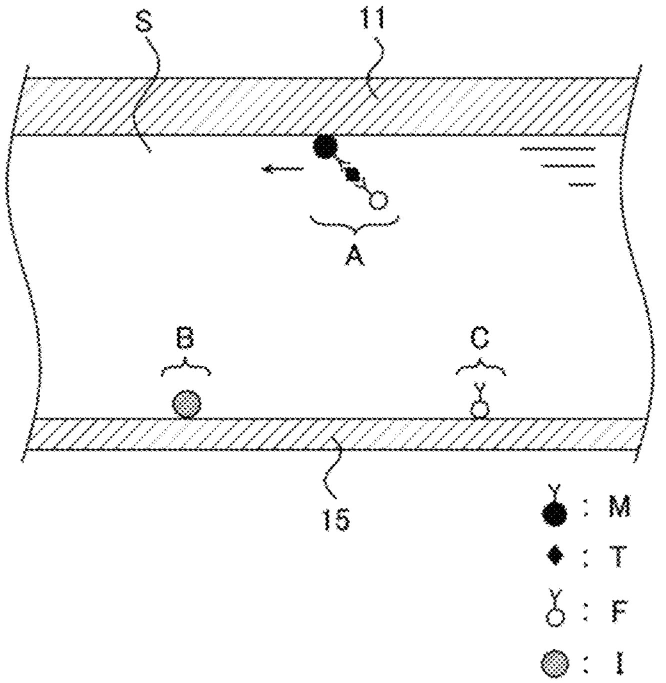
FIG. 4 is a drawing illustrating moving states of a conjugate in a conjugate moving step.

FIG. 4 illustrates moving states of a conjugate in the conjugate moving step. The conjugate is indicated as type A in the drawing, where the target substance T binds to the magnetic particles M and the fluorescent substance F in a state of being interposed therebetween.

As illustrated in FIG. 4, the conjugate is attracted to the bottom surface of the sensing plate 11 as type A, and separated from the impurity I (type B) gravitationally sedimented and non-specifically adsorbed to the liquid sample storage unit 15 and the fluorescent substance F (type C) unbound to the target substance T and gravitationally sedimented.

Therefore, the problem in that the movement of the conjugate to follow the movement of the magnetic field application unit 14 is hindered by the impurity I (type B) and the problem in that the unbound magnetic particles M which move to follow the movement of the magnetic field application unit 14 moves while involving the unbound fluorescent substance F (type C) (FIG. 2) can be prevented.

The target substance detection device 10 can thus solve the problem in that the optical signals (the positive signals) based on the conjugate whose movement is hindered by impurity I (type B) cannot be distinguished from the noise signals of unmoving type such as scratches on the bottom surface of the sensing plate 11 and fluctuation in the output of the light source, and the problem in that the moving optical signals (the false positive signals) are generated due to the unbound fluorescent substance F (type C) despite the target substance T not being present. Consequently, the detection accuracy for the target substance T can be improved while maintaining the efficient detection principle (the detection of the movement of the conjugate by the magnetic field) of the conventional external force support type sensor.

Moreover, in the target substance detection device 10, the sensing plate 11 is composed of the silicon flat plate, so that it is possible to prevent the decrease in sensitivity caused by stray light or autofluorescence and the hindrance of the movement of the conjugate as a result of the sensing plate being magnetized or becoming a magnetic shield in the conventional sensing plate structure. Hence, smooth movement of the conjugate can be ensured, and the detection accuracy for the target substance T can be significantly improved.

Since a strong magnetic field is applied to the bottom surface of the sensing plate 11 for the purpose of attracting the conjugate to the bottom surface of the sensing plate 11 and moving the conjugate against gravity in the inverted arrangement-type optical structure newly employed in the target substance detection device 10, a decrease in movement of the conjugate might occur as a result of the conjugate being caught on the bottom surface. However, the use of the silicon flat plate ensures smooth movement of the conjugate.

Figure 5:
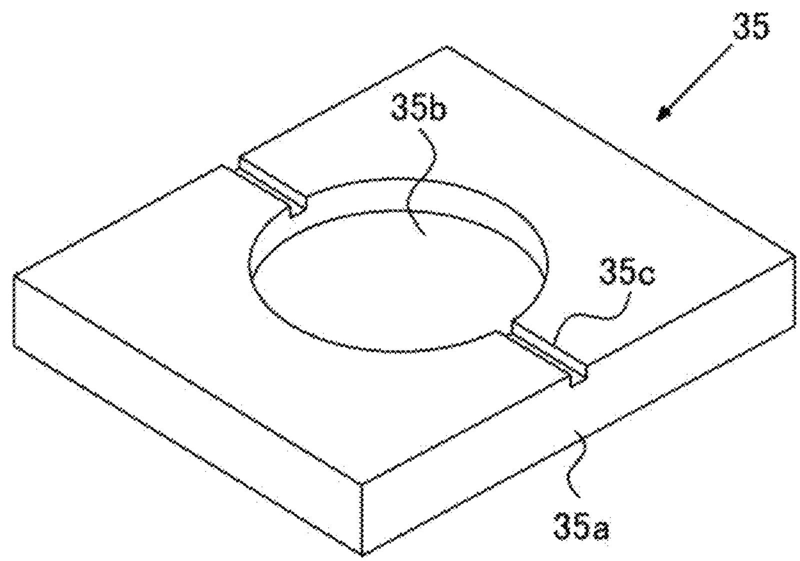
FIG. 5 is a perspective drawing illustrating a modification of a liquid sample storage unit from the top surface side.

A modification of the liquid sample storage unit 15 will be described below, with reference to FIG. 5. FIG. 5 is a perspective drawing illustrating the modification of the liquid sample storage unit from the top surface side.

As illustrated in FIG. 5, the liquid sample storage unit 35 includes a substrate 35*a*, a storage unit formed as a liquid sample reservoir unit 35*b*, and a flow path formed as a notched groove 35*c*.

With this liquid sample storage unit 35, even in a state in which the liquid sample storage unit 35 is joined to the sensing plate 11, the liquid sample can be introduced into the liquid sample reservoir unit 35*b* from outside through the notched groove 35*c*. This can improve the operability in the liquid sample storage step.

Although FIG. 3 illustrates an example in which the number of liquid sample reservoir unit 35*b* is one, a plurality of liquid sample reservoir units 35*b* may be provided to form multiple channels as another modification.

Second Embodiment

Figure 6:
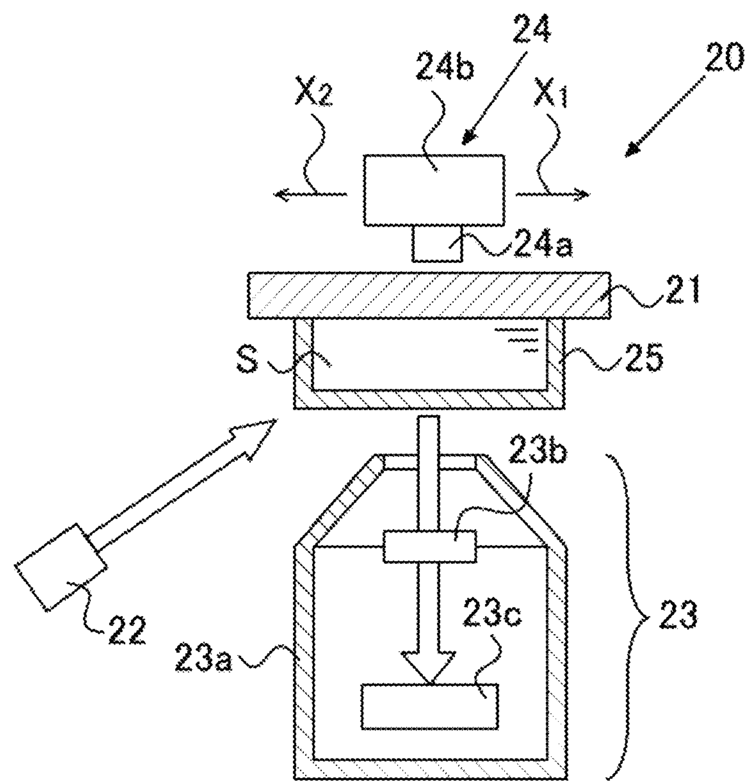
FIG. 6 is a partial sectional drawing illustrating a scheme of a target substance detection device according to a modification of a second embodiment of the present invention.
Figure 7A:
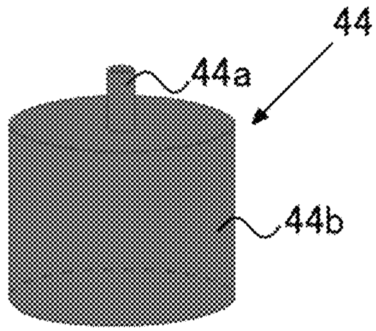
FIG. 7(*a*) is a view (1) showing an example of the structure of a magnetic field application unit having a first shape portion.
Figure 7B:
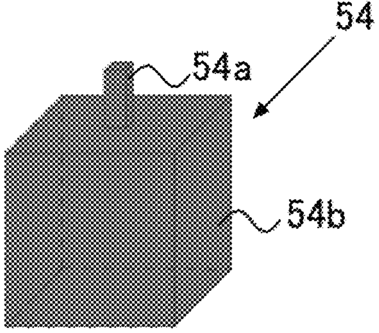
Figure 7C:
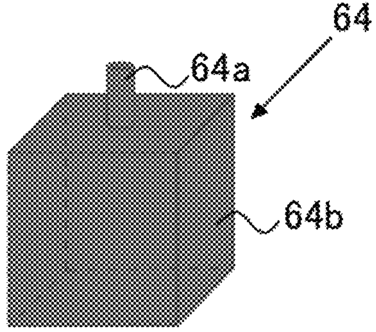
Figure 7D:
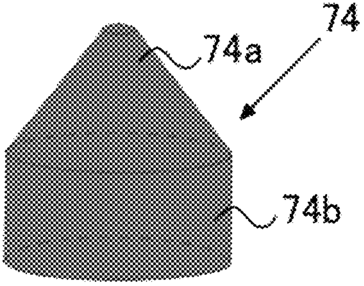
Figure 7E:
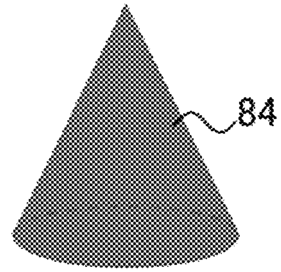

A target substance detection device according to a second embodiment of the present invention will be described below, with reference to FIG. 6. FIG. 6 is a partial sectional drawing illustrating a scheme of the target substance detection device according to the second embodiment of the present invention.

As illustrated in FIG. 6, a target substance detection device 20 includes a sensing plate 21, a light irradiation unit 22, an optical signal detection unit 23 (a housing 23*a*, an optical filter 23*b*, and an imaging device 23*c*), a magnetic field application unit 24, and a liquid sample storage unit 25.

The sensing plate 21, the light irradiation unit 22, the optical signal detection unit 23 (the housing 23*a*, the optical filter 23*b*, and the imaging device 23*c*), and the liquid sample storage unit 25 can be configured in the same way as the sensing plate 11, the light irradiation unit 12, the optical signal detection unit 13 (the housing 13*a*, the optical filter 13*b*, and the imaging device 13*c*), and the liquid sample storage unit 15 in the target substance detection device 10. Accordingly, the magnetic field application unit 24 will be described below.

The magnetic field application unit 24 is illustrated as a permanent magnet itself. The magnetic field application unit 24 is shaped as the first shape portion of an overall approximately protrusion strip shape in which a tip part 24*a* smaller in diameter than a base 24*b* protrudes from the base 24*b* and is located on the side closer to the sensing plate 21, and is movable by a moving member (not shown).

The magnetic field application unit 24 having this structure can apply a strong magnetic field to the position of the bottom surface of the sensing plate 21, as compared with the case where the permanent magnet is composed only of the base 24*b*.

In detail, with the magnetic field application unit 24, a magnetic field directed in a certain direction according to the sharp shape of the tip part 24*a* can be focused on a limited detection region on the bottom surface of the sensing plate 21 to exert strong action.

Therefore, when moving the conjugate while attracting the conjugate to the bottom surface of the sensing plate 21 against gravity, the conjugate can be prevented from being gravitationally sedimented from the position on the bottom surface of the sensing plate 21 due to insufficient strength of the applied magnetic field.

Examples of the structure of the magnetic field application unit 24 (the permanent magnet) will be described below, with reference to FIG. 7(*a*) to FIG. 7(*c*). FIG. 7(*a*) to FIG. 7(*c*) are respectively views (1) to (3) each showing an example of the structure of the magnetic field application unit (the permanent magnet) having the first shape portion.

A magnetic field application unit 44 illustrated in FIG. 7(*a*) is composed of a permanent magnet having a shape in which a cylindrical tip part 44*a* smaller in diameter than a cylindrical base 44*b* protrudes from the cylindrical base 44*b*.

A magnetic field application unit 54 illustrated in FIG. 7(*b*) is composed of a permanent magnet having a shape in which a quadrangular prism-shaped tip part 54*a* smaller in diameter than a quadrangular prism-shaped base 54*b* protrudes from the quadrangular prism-shaped base 54*b*.

A magnetic field application unit 64 illustrated in FIG. 7(*c*) is composed of a permanent magnet having a shape in which a cylindrical tip part 64*a* smaller in diameter than a quadrangular prism-shaped base 64*b* protrudes from the quadrangular prism-shaped base 64*b*.

As in these examples, the first shape portion can have any kind of structure in which a tip part of any columnar body (polygonal column, cylinder, elliptical column) protrudes from a base of any columnar body (polygonal column, cylinder, elliptical column) under the condition that the tip part is smaller in diameter (the diameter in the direction orthogonal to the protruding direction) than the base.

The advantageous effects by the magnetic field application unit 24 is achieved when a magnetic field directed in a certain direction according to the sharp shape of the permanent magnet is focused on a limited detection region on the bottom surface of the sensing plate 21 to exert strong action. Hence, further modifications illustrated in FIG. 7(*d*) and FIG. 7(*e*) are possible. FIG. 7(*d*) and FIG. 7(*e*) are respectively views (1) and (2) each showing an example of the structure of the magnetic field application unit (the permanent magnet) having the second shape portion.

A magnetic field application unit 74 illustrated in FIG. 7(*d*) is composed of a permanent magnet having a shape in which an approximately circular truncated cone-shaped second shape portion 74*a* tapered toward the sensing plate 21 is provided on a base 74*b*.

A magnetic field application unit 84 illustrated in FIG. 7(*e*) is composed of a permanent magnet having an approximately circular cone-shaped portion (a second shape portion)

As in these examples, the second shape portion can have any kind of approximately cone shape or approximately truncated cone shape under the condition that the shape tapers toward the sensing plate 21. The cone may be a polygonal cone or an elliptical cone, and the truncated cone may be a polygonal truncated cone or an elliptical truncated cone.

Figure 8:
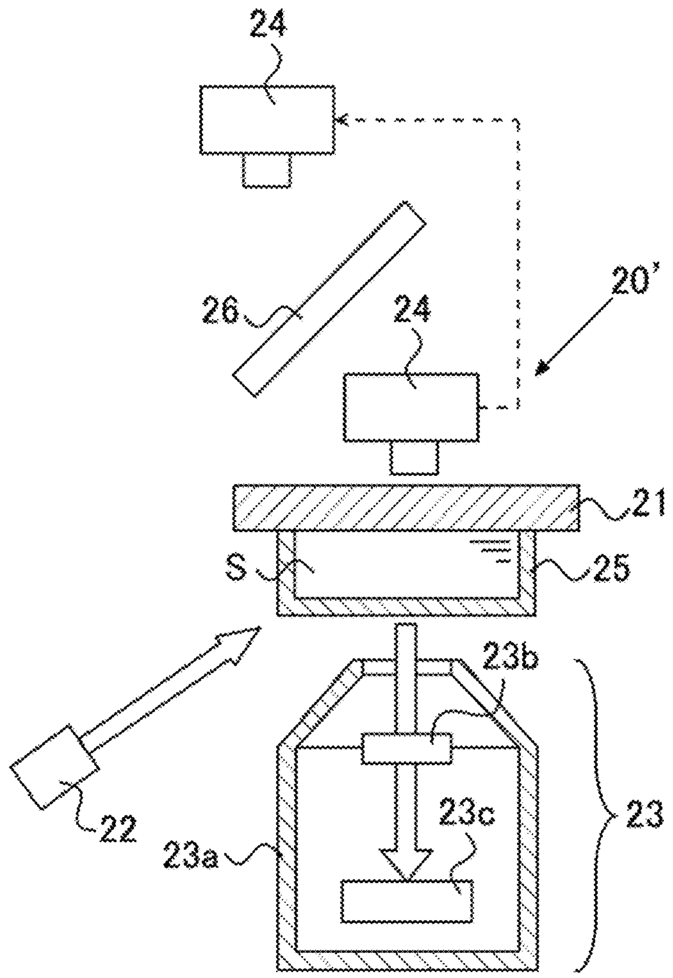
FIG. 8 is a partial sectional drawing illustrating a scheme of a target substance detection device according to a modification of the second embodiment of the present invention.

A target substance detection device according to a modification of the second embodiment of the present invention will be described below, with reference to FIG. 8. FIG. 8 is a partial sectional drawing illustrating a scheme of the target substance detection device according to the modification of the second embodiment of the present invention.

As illustrated in FIG. 8, a target substance detection device 20' differs from the target substance detection device 20 in that a magnetic shield member 26 is provided.

In the case where the magnetic shield member 26 is interposed between the magnetic field application unit 24 and the sensing plate 21, the magnetic field of the magnetic field application unit 24 applied to the sensing plate 21 is blocked, and the conjugate attracted to the bottom surface of the sensing plate 21 can be separated from the bottom surface after the measurement.

In the case where the magnetic shield member 26 is not provided, to separate the conjugate attracted to the bottom surface of the sensing plate 21, it is necessary to move the magnetic field application unit 24 to such a position where the magnetic field does not reach the sensing plate 21. In the case where the magnetic shield member 26 is provided, while the magnetic field application unit 24 is at a position where the magnetic field reaches the sensing plate 21, it is possible to separate the conjugate attracted to the bottom surface of the sensing plate 21 with the magnetic field being blocked.

Since the moving distance is shortened in this way, the moving member of the magnetic field application unit 24 can be reduced in size, and consequently the overall device can be reduced in size.

Although the magnetic shield member 26 is fixed and the magnetic field application unit 24 is moved in this modification, the magnetic shield member 26 may be a movable member that is moved to be interposed between the magnetic field application unit 24 and the sensing plate 21.

EXAMPLES

Example 1

A target substance detection device according to Example 1 was manufactured in conformity with the structure of the target substance detection device 20 illustrated in FIG. 6. The target substance detection device according to Example 1 is the inverted arrangement-type optical structure.

Specifically, the target substance detection device has the following structure. The structure of each unit will be described below, using the same reference numerals as in the target substance detection device 20 (see FIG. 6).

As the liquid sample storage unit 25, a cover glass was arranged in a frame made of silicone rubber to form a rectangular parallelepiped liquid cell having a width of 10 m, a depth of 10 mm, and a height of 1 mm.

As the sensing plate 21, a commercially available silicon flat plate made of pure silicon was surface-polished. One surface (a polished surface) of this silicon flat plate was set as a bottom surface, and a detection region on the bottom surface was surface-modified with an antifouling coating agent (KY-164 manufactured by Shin-Etsu Chemical Co., Ltd.). The surface texture of the bottom surface of the silicon flat plate will be described in detail later with reference to the drawings.

As the light irradiation unit 22, a laser diode (CPS405 manufactured by Thorlabs, Inc.) of 405 nm in wavelength was used.

As the optical signal detection unit 23, a long-pass filter (LOPF-25C-488 manufactured by Sigmakoki Co., Ltd.) as the optical filter 23*b* and the imaging device 23*c* obtained by combining a CMOS camera (acA2440-35uc manufactured by Basler AG) and a 10 times objective lens (UPLFLN10X manufactured by Olympus Corporation) were arranged in the housing 23*a*.

As the magnetic field application unit 24, the tip part 24*a* was formed of a cylindrical neodymium magnet (manufactured by Niroku Seisakusho Co., Ltd.) having a diameter of 3 mm and a height of 6 mm, the base 24*b* was formed by stacking two cylindrical neodymium magnets (manufactured by Niroku Seisakusho Co., Ltd.) having a diameter of 15 mm and a height of 10 mm so as to be 20 mm in total height, and the tip part 24*a* and the base 24*b* were connected in the height direction.

Comparative Example 1

A target substance detection device according to Comparative Example 1 was manufactured in the same way as the target substance detection device according to Example 1, except that the arrangement configuration of the liquid sample storage unit 25, the light irradiation unit 22, the optical signal detection unit 23, and the magnetic field application unit 24 with respect to the sensing plate 21 in the target substance detection device according to Example 1 of the inverted arrangement-type optical structure was vertically inverted to the upright arrangement type optical structure. That is, in the target substance detection device according to Comparative Example 1, the liquid sample storage unit 25, the light irradiation unit 22, and the optical signal detection unit 23 were located on the top surface side of the sensing plate 21, and the magnetic field application unit 24 was located on the bottom surface side of the sensing plate 21.

<Measurement Test 1>

Using the target substance detection device according to Example 1 and the target substance detection device according to Comparative Example 1, following Measurement Test 1 was conducted.

As the magnetic particles, magnetic particles (Sera-mag SpeedBead Carboxylate-Modified Magnetic Particles (Hydrophylic) manufactured by GE Healthcare) of 1 μm in particle size were modified with an antibody (Anti-Influenza A Virus Hemagglutinin H1 antibody [B219M] manufactured by abcam) using an amine coupling method. The magnetic particles were dispersed in an amount of 0.5 vol % in a 10 mM HEPES buffer solution (HEPES-NaOH (pH 7.9) manufactured by Tamagawa Seiki Co., Ltd.,) containing Tween-20, to prepare a magnetic particle dispersion liquid 1. The concentration of the magnetic particles in the magnetic particle dispersion liquid 1 was $5\times10^6$ particles/mL.

As the fluorescent substance, fluorescent particles (Fluoresbrite YG Carboxylate Microspheres 6.00 μm manufactured by Polysciences Inc.) of 6 μm in particle size were modified with an antibody (the same antibody as that used for the magnetic particles) using an amine coupling method. The fluorescent substance was dispersed in the HEPES buffer solution to prepare a fluorescent substance dispersion liquid 1. The concentration of the fluorescent substance in the fluorescent substance dispersion liquid 1 was $2\times10^6$ particles/mL.

As the liquid sample, 100 μL of the magnetic particle dispersion liquid 1, 100 μL of the fluorescent substance dispersion liquid 1, and 100 μL of the HEPES buffer solution were mixed and stirred for 1 hour, and 100 μL of the resultant liquid mixture was collected and prepared.

In Measurement Test 1, since the target substance is not contained in the liquid sample, the conjugate is not formed. Therefore, all the optical signals (the bright spots) detected by the optical signal detection unit 23 are the false positive signals derived from the fluorescent substance unbound to the conjugate. In Measurement Test 1, an edited image obtained by superimposing two-dimensional images captured over time is observed. If the moving optical signals (the bright spots) are present, their trajectories are shown in the edited image.

Figure 9:
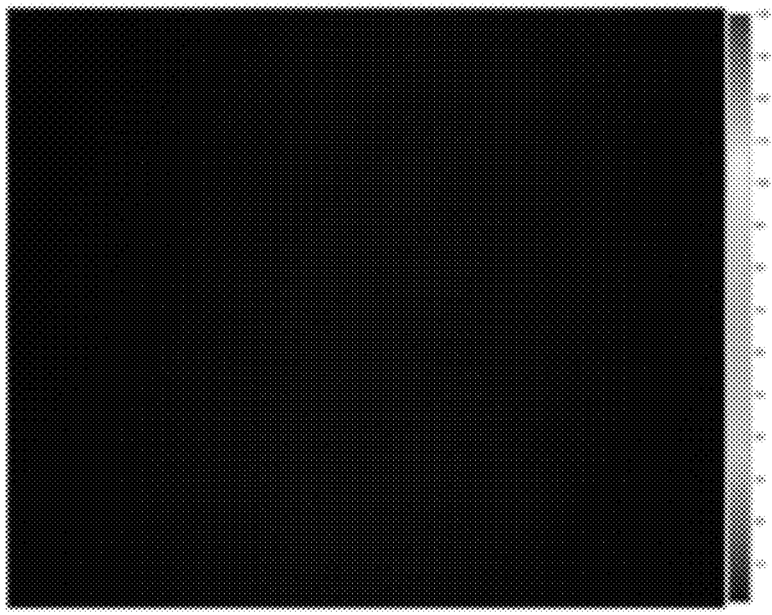
FIG. 9 is a view showing a test result of Measurement Test 1 for a target substance detection device according to Example 1.
Figure 10:
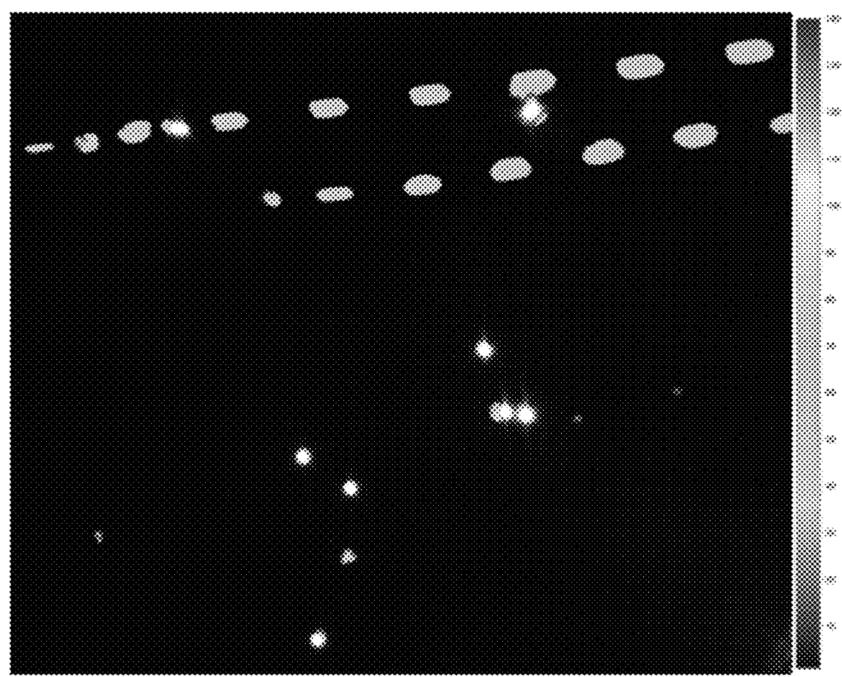
FIG. 10 is a view showing a test result of Measurement Test 1 for a target substance detection device according to Comparative Example 1.

FIG. 9 and FIG. 10 show the test results of Measurement Test 1. FIG. 9 shows the test result of Measurement Test 1 for the target substance detection device according to Example 1. FIG. 10 shows the test result of Measurement Test 1 for the target substance detection device according to Comparative Example 1.

As shown in FIG. 9, in the target substance detection device according to Example 1, the unbound fluorescent substance gravitationally sedimented and separated from the bottom surface of the sensing plate 21, so that no false positive signals were observed.

As shown in FIG. 10, in the target substance detection device according to Comparative Example 1, the gravitationally sedimented unbound fluorescent substance was involved in the movement of the unbound magnetic particles and moved, as a result of which the false positive signals were observed.

Thus, in the target substance detection device according to Example 1, the target substance can be detected more accurately than in the target substance detection device according to Comparative Example 1 as the positive signals can be distinguished from the false positive signals.

Comparative Example 2

A target substance detection device according to Comparative Example 2 was manufactured in the same way as the target substance detection device according to Example 1, except that the sensing plate 21 was formed of a transparent slide glass (White Slide Glass Edge Grinding No. 1 manufactured by Matsunami Glass Ind., Ltd.) instead of the silicon flat plate.

<Measurement Test 2>

Using the target substance detection device according to Example 1 and the target substance detection device according to Comparative Example 2, following Measurement Test 2 was conducted.

As the magnetic particles, magnetic particles (Sera-mag SpeedBead Streptavidin-Blocked Magnetic Particles manufactured by GE Healthcare) of 1 μm in particle size were used. The magnetic particles were magnetic particles surface-modified with streptavidin. The magnetic particles were dispersed in the HEPES buffer solution to prepare a magnetic particle dispersion liquid 2. The concentration of the magnetic particles in the magnetic particle dispersion liquid 2 was $5\times10^7$ particles/mL.

As the fluorescent substance, fluorescent particles (Biotin Fluoresbrite YG Microspheres 2.0 μm manufactured by Polysciences Inc.) of 2 μm in particle size were used. The fluorescent substance was a fluorescent substance surface-modified with biotin. The fluorescent substance was dispersed in the HEPES buffer solution to prepare a fluorescent substance dispersion liquid 2. The concentration of the fluorescent substance in the fluorescent substance dispersion liquid 2 was $3\times10^4$ particles/mL.

As the liquid sample, 500 μL of the magnetic particle dispersion liquid 2 and 500 μL of the fluorescent substance dispersion liquid 1 were mixed and stirred for 1 hour, and 100 μL of the resultant liquid mixture was collected and prepared.

In Measurement Test 2, although the target substance is not contained in the liquid sample, the streptavidin and the biotin specifically bind to each other, and form a pseudo conjugate by the magnetic particles and the fluorescent substance. Since this pseudo conjugate has the same moving behavior and generates the same optical signals as the conjugate obtained by binding the magnetic particles and the fluorescent substance to the target substance, Measurement Test 2 substantially corresponds to a target substance detection test.

Figure 11A:
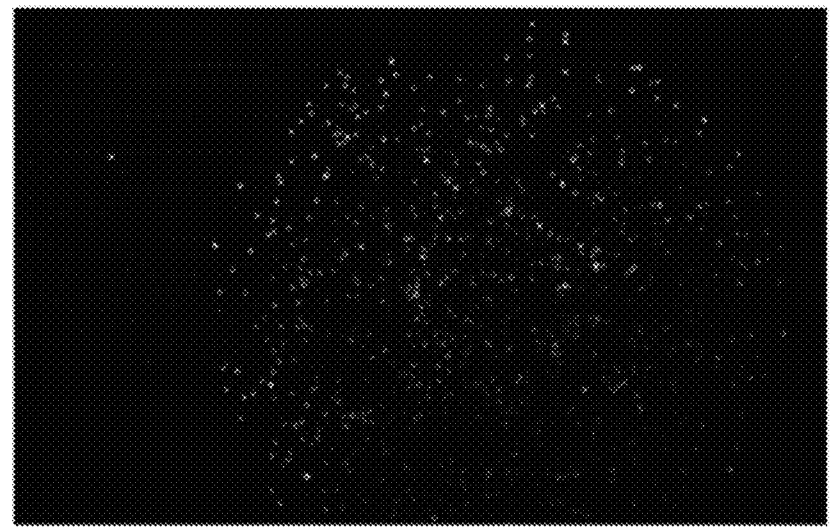
FIG. 11(*a*) is a view showing a fluorescent image as a test result of Measurement Test 2 for the target substance detection device according to Example 1.
Figure 11B:
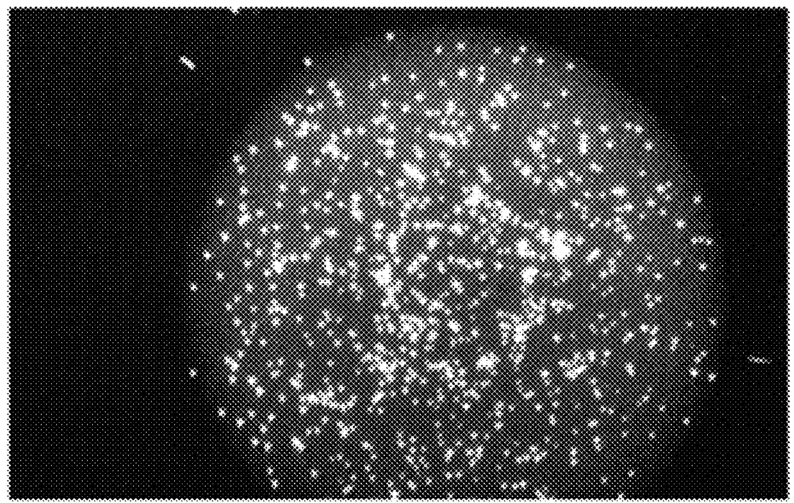

FIG. 11(*a*) and FIG. 11(*b*) show the test result of Measurement Test 2 for the target substance detection device according to Example 1. FIG. 11(*a*) is a view showing a fluorescent image as the test result of Measurement Test 2 for the target substance detection device according to Example 1. FIG. 11(*b*) is a view showing an imaging result obtained by adding a scattered light image to the fluorescent image as the test result of Measurement Test 2 for the target substance detection device according to Example 1.

Figure 12A:
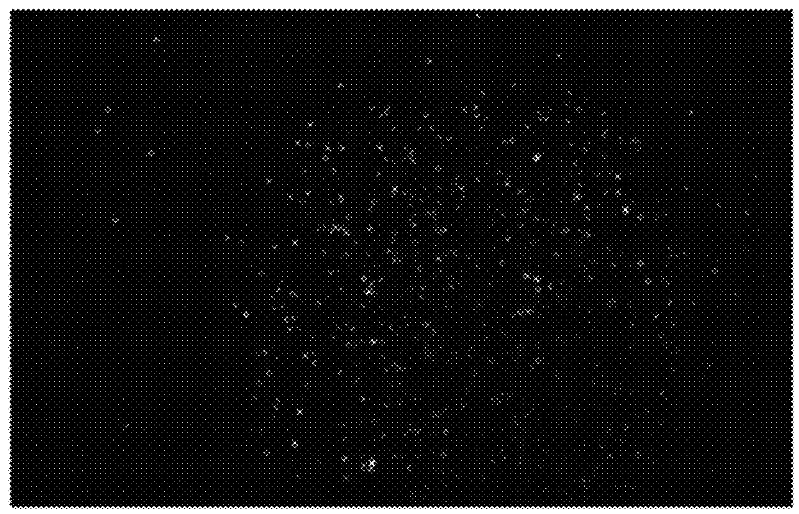
FIG. 12(*a*) is a view showing a fluorescent image as a test result of Measurement Test 2 for a target substance detection device according to Comparative Example 2.
Figure 12B:
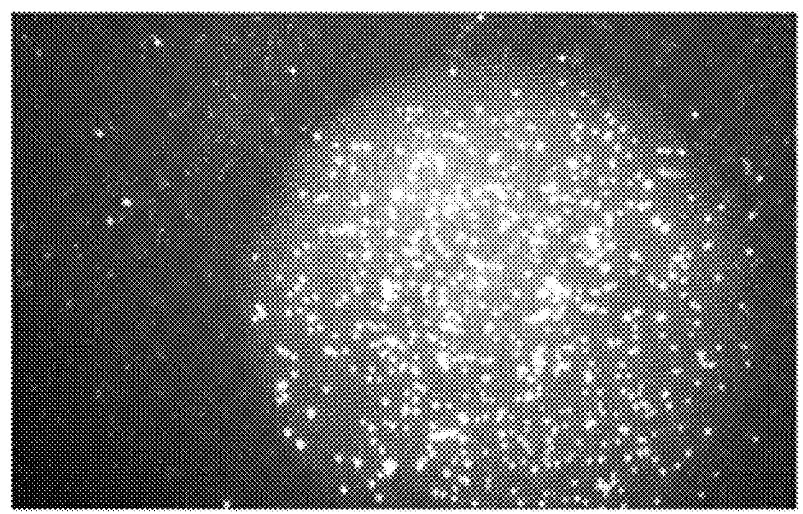

FIG. 12(*a*) and FIG. 12(*b*) show the test result of Measurement Test 2 for the target substance detection device according to Comparative Example 2. FIG. 12(*a*) is a view showing a fluorescent image as the test result of Measurement Test 2 for the target substance detection device according to Comparative Example 2. FIG. 12(*b*) is a view showing an imaging result obtained by adding a scattered light image to the fluorescent image as the test result of Measurement Test 2 for the target substance detection device according to Comparative Example 2.

These fluorescent images and imaging results obtained by adding scattered light images to the fluorescent images were acquired by selecting the presence or absence of a scattered light image on the basis of on/off operation of the optical filter 23*b*.

In the fluorescent image in the target substance detection device according to Example 1 illustrated in FIG. 11(*a*), the average of the background luminance values (12 bits) was 109. In the fluorescent image in the target substance detection device according to Comparative Example 2 illustrated in FIG. 12(*a*), the average of the background luminance values (12 bits) was 180.

In detail, in the target substance detection device according to Comparative Example 2 including the sensing plate 21 formed of the transparent slide glass, due to stray light generated from the transparent slide glass, the background luminance was higher (brighter) than in the target substance detection device according to Example 1 including the sensing plate 21 formed of the silicon flat plate. Thus, there is a possibility of whiteout of the conjugate-derived optical signals detected as the bright spots. To avoid such whiteout, choices for the fluorescent substance are likely to be limited to those that provide high luminance.

In the imaging result in the target substance detection device according to Example 1 illustrated in FIG. 11(*b*), both the bright spots by the scattered light from the magnetic particles and the bright spots by the fluorescence from the fluorescent substance were attracted to a circular range in which the magnetic field from the magnetic field application unit 24 exerted strong action.

In the imaging result in the target substance detection device according to Comparative Example 2 illustrated in FIG. 12(*b*), these bright spots were also scattered outside the circular range in which the magnetic field from the magnetic field application unit 24 exerted strong action.

In detail, in the target substance detection device according to Comparative Example 2 including the sensing plate 21 formed of the transparent slide glass, the smoothness of the bottom surface was poorer than in the target substance detection device according to Example 1 including the sensing plate 21 formed of the silicon flat plate. Hence, the movement of the pseudo conjugate was hindered as the pseudo conjugate was caught on the bottom surface.

Figure 13:
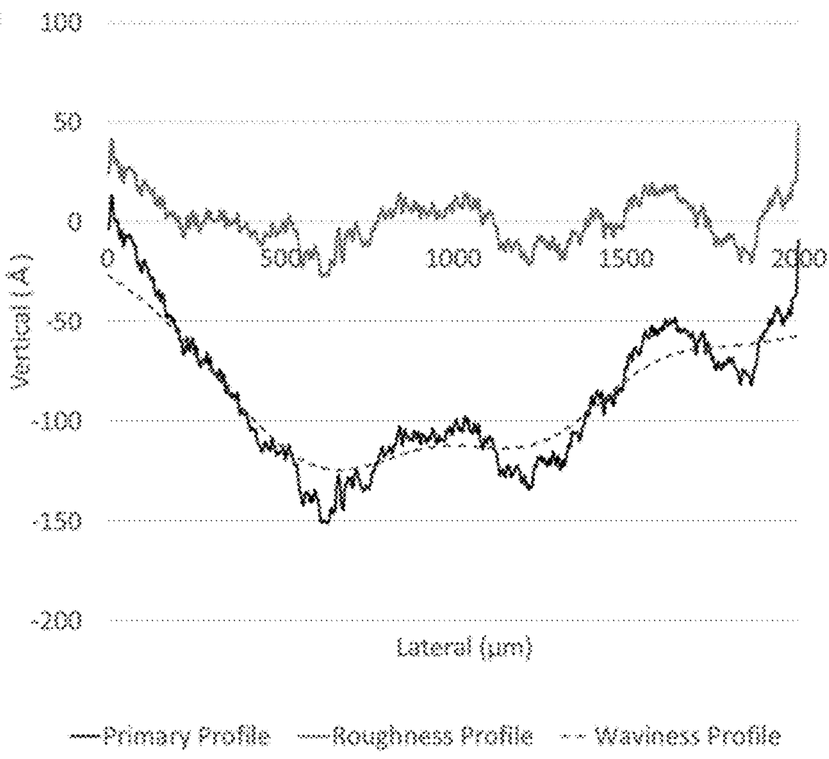
FIG. 13 is a graph showing a result of measuring the surface roughness of a silicon flat plate used in the target substance detection device according to Example 1.
Figure 14:
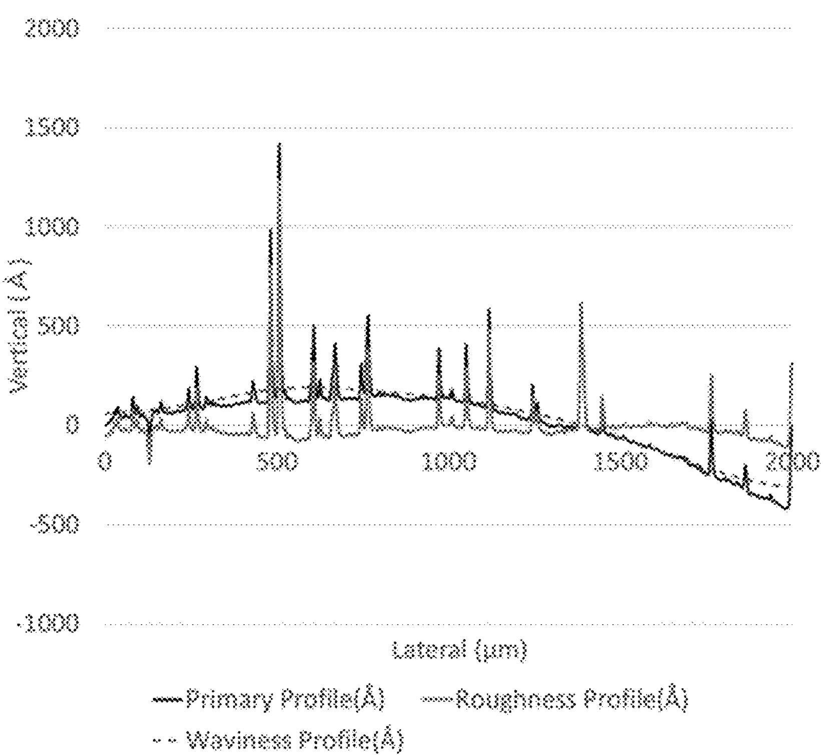
FIG. 14 is a graph showing a result of measuring the surface roughness of a transparent slide glass used in the target substance detection device according to Comparative Example 2.

Regarding this, FIG. 13 shows the result of measuring the surface roughness of the silicon flat plate used in the target substance detection device according to Example 1, and FIG. 14 shows the result of measuring the surface roughness of the transparent slide glass used in the target substance detection device according to Comparative Example 2.

The surface roughness was measured by a measurement method in accordance with JIS B0601-2013, using a profilometer (Dektak XT-S manufactured by Bruker Corporation).

The measurement was performed on the surface part not surface-modified with the antifouling coating agent, for both the silicon flat plate and the transparent slide glass. Three sections each of which is a region of a straight section of 2 mm in length in the surface part were set, and subjected to the measurement.

The surface roughness was determined as Ra (arithmetic mean roughness) using software attached to the profilometer.

Moreover, the maximum height roughness Rz was actually measured.

Ra (arithmetic mean roughness) of the silicon flat plate used in the target substance detection device according to Example 1 was 1.5 nm or less in each of the three sections (1.308 nm, 0.953 nm, 1.012 nm). Regarding the maximum height roughness Rz, the maximum value in the three sections was 21.5 nm.

Ra (an arithmetic mean roughness) of the transparent slide glass used in the target substance detection device according to Comparative Example 2 was more than 4.5 nm in each of the three sections (4.590 nm, 5.029 nm, 4.861 nm). Regarding the maximum height roughness Rz, the maximum value in the three sections was 184.0 nm.

Typically, the quality of the surface texture of an optically polished flat plate is evaluated based on a criterion of whether the maximum height determined by interference fringe measurement using a He—Ne laser with a wavelength of 633 nm ($\lambda$=633 nm) is 63.3 nm or less ($\lambda$/10 or less). In the case of performing the evaluation using a profilometer, the value of the maximum height roughness Rz corresponds to the value of the maximum height (63.3 nm or less).

For the sensing plate 21, if the maximum height roughness Rz is less than 184.0 nm, the hinderance of the movement of the conjugate can be alleviated. However, the maximum height roughness Rz is preferably 63.3 nm or less (λ/10 or less) according to the criterion. Anyway, such silicon flat plates are widely distributed in semiconductor applications and can be obtained at low costs.

Reference Example 1

A target substance detection device according to Reference Example 1 was manufactured in the same way as the target substance detection device according to Example 1, except that the magnetic field application unit 24, which was obtained in such a manner that the tip part 24*a* was formed of a cylindrical neodymium magnet (manufactured by Niroku Seisakusho Co., Ltd.) having a diameter of 3 mm and a height of 6 mm, the base 24*b* was formed by stacking two cylindrical neodymium magnets (manufactured by Niroku Seisakusho Co., Ltd.) having a diameter of 15 mm and a height of 10 mm so as to be 20 mm in total height, and the tip part 24*a* and the base 24*b* were connected in the height direction, was changed to the following magnetic field application unit.

In the target substance detection device according to Reference Example 1, instead of the magnetic field application unit 24, a reference magnetic field application unit obtained by simply connecting four cylindrical neodymium magnets having a diameter of 3 mm and a height of 6 mm (i.e. the foregoing cylindrical neodymium magnet of the tip part 24*a*) in the height direction.

Using the target substance detection device according to Example 1 and the target substance detection device according to Reference Example 1, the same test as Measurement Test 2 was conducted.

In this test, to compare the magnetic field action between the magnetic field application unit 24 and the reference magnetic field application unit, respective fluorescent images 30 seconds and 60 seconds after each magnetic field application unit was placed at the initial position and the collection of the pseudo conjugate was started were observed. The same liquid sample was used in the test.

Figure 15A:
FIG. 15(*a*) is a view showing a fluorescent image 30 seconds after collection start in the target substance detection device according to Example 1.
Figure 15B:

FIG. 15(*a*) shows a fluorescent image 30 seconds after the collection start in the target substance detection device according to Example 1. FIG. 15(*b*) shows a fluorescent image 60 seconds after the collection start in the target substance detection device according to Example 1.

Figure 16A:
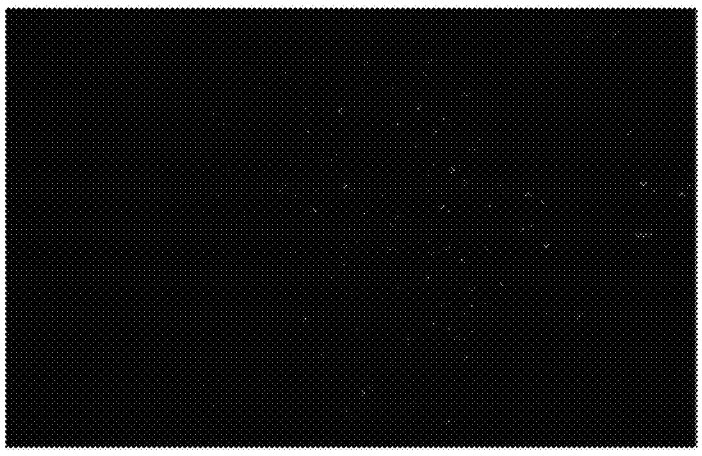
FIG. 16(*a*) is a view showing a fluorescent image 30 seconds after collection start in a target substance detection device according to Reference Example 1.
Figure 16B:

FIG. 16(*a*) shows a fluorescent image 30 seconds after the collection start in the target substance detection device according to Reference Example 1. FIG. 16(*b*) shows a fluorescent image 60 seconds after the collection start in the target substance detection device according to Reference Example 1.

Based on FIG. 15(*a*), in the target substance detection device according to Example 1, 306 of the bright spots were observed in the fluorescent image 30 seconds after the collection start.

Based on FIG. 16(*a*), in the target substance detection device according to Reference Example 1, only 192 of the bright spots were observed in the fluorescent image 30 seconds after the collection start.

Based on FIG. 15(*b*), in the target substance detection device according to Example 1, 472 of the bright spots were observed in the fluorescent image 60 seconds after the collection start.

Based on FIG. 16(*b*), in the target substance detection device according to Reference Example 1, only 269 of the bright spots were observed in the fluorescent image 60 seconds after the collection start.

No difference in the diameter of the circular region for collecting the pseudo conjugate was found between the magnetic field application unit 24 and the reference magnetic field application unit, and the target substance detection device according to Example 1 was able to collect the pseudo conjugate in the detection region more efficiently than the target substance detection device according to Reference Example 1 both 30 seconds and 60 seconds after the collection start.

When the magnetic flux density at a position 5 mm away from each of the tip of the magnetic field application unit 24 and one end of the reference magnetic field application unit was measured by a magnetic flux density meter (Teslameter manufactured by Nihon Denji Sokki Co., Ltd.), the magnetic flux density was 123 mT in the magnetic field application unit 24, and 28 mT in the reference magnetic field application unit.

These results indicate that the magnetic field application unit 24 in the target substance detection device according to Example 1, while maintaining a narrow circular region for collecting the pseudo conjugate, was able to enhance the magnetic flux density in the region.

DESCRIPTION OF REFERENCE NUMERALS

10, 20, 20' target substance detection device
11, 21, 101 sensing plate
12, 22, 102 light irradiation unit
13, 23, 103 optical signal detection unit
13*a*, 23*a* housing
13*b*, 23*b* optical filter
13*c*, 23*c*, 103*c* imaging device
14, 24, 44, 54, 64, 74, 84, 104 magnetic field application unit
15, 25, 35 liquid sample storage unit
24*a*, 44*a*, 54*a*, 64*a*, 74*a* tip part
24*b*, 44*b*, 54*b*, 64*b*, 74*b* base
26 magnetic shield member
35*a* substrate
35*b* liquid sample reservoir unit
35*c* notched groove
103*a* half mirror
103*b* objective lens
S liquid sample
M magnetic particles
T target substance
F fluorescent substance
I impurity
$X_1$, $X_2$ direction

The invention claimed is:

1. A target substance detection device comprising:

a liquid sample storage unit that is partially or wholly formed of a transparent member, and includes a storage unit formed so as to be open at a top surface thereof and configured to store a liquid sample containing a fluorescent substance and magnetic particles that form a conjugate with a target substance;

a sensing plate composed of a silicon flat plate whose bottom surface is a smooth surface, the bottom surface being joined to the top surface of the liquid sample storage unit;

a light irradiation unit configured to irradiate the bottom surface of the sensing plate with light including an excitation wavelength of the fluorescent substance, via the liquid sample storage unit; and a magnetic field application unit located on a top surface side of the sensing plate, and configured to move a permanent magnet in a direction having a vector component in a direction parallel to an in-plane direction of the bottom surface of the sensing plate in a state in which a magnetic field is applied to the conjugate in the liquid sample stored in the storage unit.

2. The target substance detection device according to claim 1, wherein maximum height roughness Rz indicating roughness of the smooth surface is 63.3 nm or less.

3. The target substance detection device according to claim 1, wherein the permanent magnet includes any of a first shape portion and a second shape portion, the first shape portion being a portion of an overall approximately protrusion strip shape in which a tip part smaller in diameter than a base protrudes from the base and is located on a side closer to the sensing plate, and the second shape portion being a portion of an approximately cone shape or an approximately truncated cone shape tapered toward the sensing plate.

4. The target substance detection device according to claim 1, comprising a magnetic shield member configured to be interposed between the sensing plate and the magnetic field application unit as a result of movement of the magnetic shield member or the magnetic field application unit.

5. The target substance detection device according to claim 1, comprising an optical signal detection unit located on a bottom surface side of the sensing plate, and configured to detect fluorescence emitted from the fluorescent substance.

6. The target substance detection device according to claim 5, wherein the optical signal detection unit includes an optical filter configured to transmit light included in a wavelength band of the fluorescence emitted from the fluorescent substance.

7. The target substance detection device according to claim 1, wherein the smooth surface is surface-modified with a coating agent that suppresses adsorption of the conjugate.

8. The target substance detection device according to claim 1, wherein the liquid sample storage unit includes a liquid sample flow path connecting an outside of the liquid sample storage unit and the storage unit.

9. A target substance detection method of detecting a target substance using the target substance detection device according to claim 1, the target substance detection method comprising:

a liquid sample storage step of storing, in the storage unit in the liquid sample storage unit, a liquid sample containing a fluorescent substance and magnetic particles that form a conjugate with a target substance;

a separation step of placing the magnetic field application unit at an initial position on the top surface side of the sensing plate, and attracting the conjugate in the liquid sample to the bottom surface of the sensing plate to separate the conjugate from gravitational sediments in the liquid sample;

a light irradiation step of irradiating the bottom surface of the sensing plate with light including an excitation wavelength of the fluorescent substance from the light irradiation unit via the liquid sample storage unit; and a conjugate moving step of, in a state in which the bottom surface of the sensing plate is irradiated with the light, moving the magnetic field application unit from the initial position in a direction having a vector component in a direction parallel to an in-plane direction of the bottom surface of the sensing plate, to move the conjugate attracted to the bottom surface of the sensing plate in the direction parallel to the in-plane direction of the bottom surface.

* * * * *